(12) United States Patent
Morrison et al.

(10) Patent No.: US 9,561,245 B2
(45) Date of Patent: Feb. 7, 2017

(54) COMBINATION TREATMENTS FOR MELANOMA

(71) Applicant: The Board of Regents of the University of Texas System, Austin, TX (US)

(72) Inventors: Sean Morrison, Dallas, TX (US); Elena Piskounova, Dallas, TX (US); Ugur Eskiocak, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 230 days.

(21) Appl. No.: 14/019,327

(22) Filed: Sep. 5, 2013

(65) Prior Publication Data

US 2014/0066392 A1    Mar. 6, 2014

Related U.S. Application Data (60) Provisional application No. 61/697,696, filed on Sep. 6, 2012, provisional application No. 61/702,000, filed on Sep. 17, 2012.

(51) Int. Cl.

| | |
|---|---|
| *A61K 31/7048* | (2006.01) |
| *A61K 31/585* | (2006.01) |
| *A61K 31/506* | (2006.01) |
| *A61K 31/437* | (2006.01) |
| *A61K 31/404* | (2006.01) |

(52) U.S. Cl.
CPC ......... *A61K 31/7048* (2013.01); *A61K 31/404* (2013.01); *A61K 31/437* (2013.01); *A61K 31/506* (2013.01); *A61K 31/585* (2013.01)

(58) Field of Classification Search
None
See application file for complete search history.

(56) References Cited

U.S. PATENT DOCUMENTS

| | | | |
|---|---|---|---|
| 6,071,885 A | 6/2000 | Florkiewicz | |
| 2004/0061142 A1 | 4/2004 | Raman et al. | |
| 2006/0009482 A1 | 1/2006 | Tomai et al. | |
| 2006/0009492 A1 | 1/2006 | Zhimin | |
| 2006/0205679 A1 | 9/2006 | Streeper et al. | |
| 2007/0248537 A1 | 10/2007 | Yang et al. | |
| 2008/0004271 A1* | 1/2008 | McKenna et al. | 514/234.2 |
| 2008/0038770 A1 | 2/2008 | Hansford et al. | |
| 2008/0200401 A1 | 8/2008 | Addington | |
| 2009/0275546 A1 | 11/2009 | Signore et al. | |
| 2010/0081654 A1 | 4/2010 | Stockwell et al. | |
| 2010/0184033 A1 | 7/2010 | West et al. | |
| 2010/0239656 A1 | 9/2010 | Astsaturov et al. | |
| 2010/0317541 A1 | 12/2010 | Addington et al. | |
| 2012/0059021 A1 | 3/2012 | Biechele et al. | |
| 2012/0070438 A1 | 3/2012 | Hoey et al. | |
| 2012/0122807 A1 | 5/2012 | Shraibom | |
| 2014/0080772 A1 | 3/2014 | Morrison et al. | |
| 2015/0023915 A1 | 1/2015 | Morrison et al. | |

FOREIGN PATENT DOCUMENTS

| | | |
|---|---|---|
| JP | 2008/079610 | 4/2008 |
| WO | WO 97/04761 | 2/1997 |
| WO | WO 2004/043340 | 5/2004 |
| WO | WO 2008/123266 | 10/2008 |
| WO | WO 2009/064657 | 5/2009 |
| WO | WO 2009/076170 | 6/2009 |
| WO | WO 2010/068247 | 6/2010 |
| WO | WO 2011/062927 | 5/2011 |
| WO | WO 2011/068876 | 6/2011 |
| WO | WO 2011/133668 | 10/2011 |
| WO | WO 2013-044169 | 3/2013 |
| WO | WO 2014-039741 | 3/2014 |
| WO | WO 2015-009591 | 1/2015 |

OTHER PUBLICATIONS

Martinez, A., Castro, A., Dorronsoro, I., & Alonso, M. (2002). Glycogen synthase kinase 3 (GSK-3) inhibitors as new promising drugs for diabetes, neurodegeneration, cancer, and inflammation. Medicinal research reviews, 22(4), 373-384.*

Chapman el al., "Improved survival with vemurafenib in melanoma with BRAF V600E mutation", *N Engl J Med.*, 364(26); 2507-2516, 2011.

PCT International Search Report and Written Opinion issued in International Application No. PCT/US13/58372, mailed Jan. 10, 2014.

PCT International Search Report and Written Opinion issued in International Application No. PCT/US13/58374, mailed Jan. 16, 2014.

Fliri et al., "Drug effects viewed from a signal transduction network perspective", *Journal of Medicinal Chemistry*, 52(24):8038-8046, 2009.

(Continued)

*Primary Examiner* — Shaojia Anna Jiang
*Assistant Examiner* — Dale R Miller
(74) *Attorney, Agent, or Firm* — Parker Highlander PLLC (57) ABSTRACT

The present invention relates to combination therapies for melanoma, and in particular, metastatic melanoma. Drugs for use in such therapies in include BRAF inhibitors such as PLX 4720 and PLX 4734 in combination with RO 31-8220, bafetinib or cardiac glycosides.

19 Claims, 4 Drawing Sheets
(4 of 4 Drawing Sheet(s) Filed in Color)

(56) References Cited

OTHER PUBLICATIONS

Isoldi et al., "The role of calcium, calcium-activated K+ channels, and tyrosine/kinase in psoralen-evoked responses in human melanoma cells", *Brazilian Journal of Medicine and Biological Research*, 37:559-568, 2004.
Krasagakis et al., "Proliferation of human melanoma cells is under tight control of protein kinase C alpha", *Journal of Cellular Physiology*, 199:381-387, 2004.
López-Lázaro et al., "Digitoxin inhibits the growth of cancer cell lines at concentrations commonly found in cardiac patients", *J Nat Prod.*, 68:1642-1645, 2005.
Stavroulake et al., "Exposure of normal human melanocytes to a tumor promoting phorbol ester reverses growth suppression by transforming growth factor beta", *J Cell Physiol.*, 214:363-370, 2008.
PCT International Search Report and Written Opinion issued in International Application No. PCT/US2014/046464, mailed Jan. 22, 2015.

\* cited by examiner

COMBINATION TREATMENTS FOR MELANOMA

The present application claims benefit of priority to U.S. Provisional Application Ser. No. 61/697,696, filed Sep. 6, 2012, and Ser. No. 61/702,000, filed Sep. 17, 2012, the entire contents of both applications being hereby incorporated by reference.

BACKGROUND OF THE INVENTION

I. Technical Field

The present invention relates generally to the fields of medicine and oncology genetics. More particularly, it relates to the use of chemical entities, alone or in combination, to treat melanoma, particularly metastatic melanoma.

II. Related Art

Melanoma is a malignant tumor of melanocytes. Melanocytes are cells that produce the dark pigment, melanin, which is responsible for the color of skin. They predominantly occur in skin, but are also found in other parts of the body, including the bowel, oral cavity and the eye. Melanin also protects the deeper layers of the skin from the sun's harmful ultraviolet (UV) rays. When people spend time in the sunlight, the melanocytes make more melanin and cause the skin to tan. This also happens when skin is exposed to other forms of ultraviolet light (such as in a tanning booth). If the skin receives too much ultraviolet light, the melanocytes may begin to grow abnormally and become cancerous, leading to melanoma.

Because of the link to sun exposure, the chance of getting melanoma increases with age, but many young people age also get melanoma. In fact, melanoma is one of the most common cancers in young adults. Each year in the U.S., more than 50,000 people—young and old—learn that they have melanoma. And, according to a WHO report, about 48,000 melanoma related deaths occur worldwide each year. The treatment includes surgical removal of the tumor, and if melanoma is found early while relatively small and thin, complete removal gives a high cure rate. The chance of the melanoma coming back or spreading depends on how deeply it has invaded into the layers of the skin, and thus, the more progressed the lesion, the great the chancer for recurrence and/or metastasis. For melanomas that recur or spread, treatments include chemo-plus immunotherapy or radiation therapy, but the prognosis for such patients, including those exhibiting metastatic disease (AJCC Stage III and IV) is poor, with 5-year survival rates being less than 10%. As such, improved treatments for melanoma, particularly for advanced metastatic disease, are urgently needed.

SUMMARY OF THE INVENTION

Thus, in accordance with the present invention, there is provided a method of inhibiting melanoma in a subject comprising administering to the subject (a) a BRAF inhibitor; and (b) a cardiac glycoside, RO31-8220 or bafetinib, in an amount sufficient to inhibit the melanoma. Specific combinations include a BRAF inhibitor and a cardiac glycoside; a BRAF inhibitor and bafetinib; and a BRAF inhibitor and RO31-8220.

The subject may be a human or a non-human mammal. Inhibiting may comprise inhibiting the growth of primary melanomas, inhibiting the formation of metastases, inhibiting the growth of metastases, killing circulating melanoma cells, inducing remission, extending remission, or inhibiting recurrence. The melanoma may be AJCC stage III disease or AJCC stage IV disease. The subject may have previously received a radiotherapy, a chemotherapy, an immunotherapy, a molecularly targeted therapy, such as BRAF or MEK inhibitor, or had surgical resection of a tumor.

The BRAF inhibitor may be administered before the other therapy, at the same time as the other therapy, or after the other therapy. The BRAF inhibitor may be administered more than once. The cardiac glycoside, RO31-8220 or bafetinib may be administered more than once. The cardiac glycoside may be selected from digoxin, digitoxin, gitoxin, oleandrin, neriifolin, bufalin, marinobufagenin, cinobufagenin, UNBS1450 and lanatoside C. The BRAF inhibitor may be PLX 4032, PLX 4720 or PLX 4734.

Administering may comprise intravenous, intraarterial, subcutaneous, oral or intra-tumoral administration. Administering may also comprise local, regional or systemic administration. Administering may comprise continuous infusion over a period of time. The subject may have failed one or more standard melanoma therapies. The amount may be sufficient to inhibit the melanoma is less than the amount required for inhibition by any single agent alone. The amount may be sufficient to inhibit the melanoma is less toxic than the amount required for inhibition by any single agent alone.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-B. Effect of Digitoxin on in vivo tumor growth. FIG. 1A, M481 tumor-growth curves of digitoxin and/or BRAF inhibitor (PLX 4720) treated mice. M481 metastatic melanoma cells were implanted in s.c. tissue on right flanks of NSG mice. When tumors became palpable mice were i.p. injected with digitoxin (0.5 mg/kg) or DMSO. For PLX4720 treatment mice were switched to either a chow diet containing 417 mg/kg PLX4720 or the control chow containing no compound. Tumors were measured every 2-3 day with calipers. Mean±SD is reported (* $P<0.05$, *** $P<0.0005$, ns: not significant; two-tailed Student's t test).

FIGS. 2A-B. Effect of RO 31-8220 on in vivo tumor growth. FIG. 2B, Representative bioluminescence images of melanomas at day 14.

FIGS. 3A-B. Effect of Bafetinib on in vivo tumor growth.

FIG. 4. Effect of Digitoxin and/or PLX4720 on in vivo tumor growth using primary melanomas isolated from three patients. M481, M487 and M610 melanoma cells carrying BRAF V600E mutations were implanted in s.c. tissue on right flanks of NSG mice. When tumors became palpable, mice were randomized to four different treatments. Mice were treated either with digitoxin (0.5 mg/kg/day in 200 μl of 0.5% promethylcellulose, 0.2% Tween80 and 5% DMSO by oral gavage), or PLX4720 (20 mg/kg/day in 200 μl of 1% carboxymethyl cellulose and 5% DMSO by oral gavage) alone, or in combination. Control mice received vehicle only (200 μl 0.5% promethylcellulose, 0.2% Tween80 and 5% DMSO per day). Tumors were measured every 2-3 days with calipers.

DETAILED DESCRIPTION OF THE INVENTION

The inventors have identified BRAF inhibitors and other agents useful in combination treatments of melanoma, including stage III and IV disease, as well as metastatic disease. Specific combinations of BRAF inhibitors plus Lyn inhibitors, PKC inhibitors plus BRAF inhibitors, and cardiac glycosides plus BRAF inhibitors are contemplated.

I. Cancer Therapeutic Agents

A. Cardiac Glycosides

Cardiac glycosides are drugs used in the treatment of congestive heart failure and cardiac arrhythmia. These glycosides are found as secondary metabolites in several plants, but also in some animals, such as the milkweed butterflies. Therapeutic uses of cardiac glycosides primarily involve the treatment of cardiac failure. Their utility results from an increased cardiac output by increasing the force of contraction. By increasing intracellular calcium as described below, cardiac glycosides increase calcium-induced calcium release and thus contraction.

Drugs such as ouabain and digoxin are cardiac glycosides. Digoxin from the foxglove plant is used clinically, whereas ouabain is used only experimentally due to its extremely high potency.

Normally, sodium-potassium pumps in the membrane of cells (in this case, cardiac myocytes) pump potassium ions in and sodium ions out. Cardiac glycosides inhibit this pump by stabilizing it in the E2-P transition state, so that sodium cannot be extruded: intracellular sodium concentration therefore increases. A second membrane ion exchanger, NCX, is responsible for 'pumping' calcium ions out of the cell and sodium ions in (3Na/Ca); raised intracellular sodium levels inhibit this pump, so calcium ions are not extruded and will also begin to build up inside the cell.

Increased cytoplasmic calcium concentrations cause increased calcium uptake into the sarcoplasmic reticulum via the SERCA2 transporter. Raised calcium stores in the SR allow for greater calcium release on stimulation, so the myocyte can achieve faster and more powerful contraction by cross-bridge cycling. The refractory period of the AV node is increased, so cardiac glycosides also function to regulate heart rate.

Binding of cardiac glycoside to Na—K ATPase is slow, and also, after binding, intracellular calcium increases gradually. Thus, the action of digitalis (even on IV injection) is delayed.

Raised extracellular potassium decreases binding of cardiac glycoside to Na—K ATPase. Consequently, increased toxicity of these drugs is observed in the presence of Hypokalemia.

1. Digoxin

Digoxin is a purified cardiac glycoside extracted from the foxglove plant, *Digitalis lanata*. Its corresponding aglycone is digoxigenin, and its acetyl derivative is acetyldigoxin. Digoxin is widely used in the treatment of various heart conditions, namely atrial fibrillation, atrial flutter and sometimes heart failure that cannot be controlled by other medication. Digoxin preparations are commonly marketed under the trade names Lanoxin, Digitek, and Lanoxicaps. It is also available as a 0.05 mg/ml oral solution and 0.25 mg/ml or 0.5 mg/ml injectable solution. It is marketed by GlaxoSmithKline and many other pharmaceutical manufacturers.

Today, the most common indications for digoxin are atrial fibrillation and atrial flutter with rapid ventricular response. Beta blockers and/or calcium channel blockers should be the first choice. High ventricular rate leads to insufficient diastolic filling time. By slowing down the conduction in the AV node and increasing its refractory period, digoxin can reduce the ventricular rate. The arrhythmia itself is not affected, but the pumping function of the heart improves owing to improved filling.

The use of digoxin in heart problems during sinus rhythm was once standard, but is now controversial. In theory, the increased force of contraction should lead to improved pumping function of the heart, but its effect on prognosis is disputable, and other effective treatments are now available. Digoxin is no longer the first choice for congestive heart failure, but can still be useful in patients who remain symptomatic despite proper diuretic and ACE inhibitor treatment.

Digitalis/digoxin has recently fallen out of favor because it did not demonstrate a mortality benefit in patients with congestive heart failure; however, it did demonstrate a reduction in hospitalizations for this condition. Because other therapies have shown a mortality benefit in congestive heart failure, maximizing other therapies (e.g., beta blockers) first is recommended before using digoxin.

Digoxin is usually given by mouth, but can also be given by IV injection in urgent situations (the IV injection should be slow, and heart rhythm should be monitored). While IV therapy may be better tolerated (less nausea), digoxin has a very long distribution half-life into the cardiac tissue, which will delay its onset of action by a number of hours. The half-life is about 36 hours, and digoxin is given once daily, usually in 125-m or 250-1.1 g doses.

In patients with decreased kidney function, the half-life is considerably longer, calling for a reduction in dose or a switch to a different glycoside, such as digitoxin (not available in the United States), which has a much longer elimination half-life of around seven days, but is mainly eliminated from the body via the liver, and thus not affected by changes in kidney function.

Effective plasma levels vary depending on the medical indication. For congestive heart failure, levels between 0.5 and 1.0 ng/ml are recommended. This recommendation is based on post hoc analysis of prospective trials, suggesting higher levels may be associated with increased mortality rates. For heart rate control (atrial fibrillation), plasma levels are less defined and are generally titrated to a goal heart rate. Typically, digoxin levels are considered therapeutic for heart rate control between 1.0 and 2.0 ng/ml. In suspected toxicity or ineffectiveness, digoxin levels should be monitored. Plasma potassium levels also need to be closely controlled (see side effects below).

Quinidine, verapamil, and amiodarone increases plasma levels of digoxin (by displacing tissue binding sites and depressing renal digoxin clearance), so plasma digoxin must be monitored carefully.

The occurrence of adverse drug reactions is common, owing to its narrow therapeutic index (the margin between effectiveness and toxicity). Adverse effects are concentration-dependent, and are rare when plasma digoxin concentration is <0.8 μg/l. They are also more common in patients with low potassium levels (hypokalemia), since digoxin normally competes with $K^+$ ions for the same binding site on the $Na^+/K^+$ ATPase pump.

Common adverse effects (≥1% of patients) include: loss of appetite, nausea, vomiting and diarrhea as gastrointestinal motility increases. Other common effects are blurred vision, visual disturbances (yellow-green halos and problems with color perception), confusion, drowsiness, dizziness, insomnia, nightmares, agitation, and depression, as well as a higher acute sense of sensual activities. Less frequent adverse effects (0.1%-1%) include: acute psychosis, delirium, amnesia, convulsions, shortened QRS complex, atrial or ventricular extrasystoles, paroxysmal atrial tachycardia with AV block, ventricular tachycardia or fibrillation, and heart block. Rarely, digoxin has been shown to cause thrombocytopenia. Gynaecomastia (enlargement of breast tissue) is mentioned in many textbooks as a side effect, thought to be due to the estrogen-like steroid moiety of the digoxin molecule, but when systematically sought, the evidence for this is equivocal. The pharmacological actions of digoxin usually result in non-toxic electrocardiogram changes, including ST depression or T wave inversion. PR interval prolongation, however, may be a sign of digoxin toxicity. Additionally, increased intracellular $Ca^{2+}$ may cause a type of arrhythmia called bigeminy (coupled beats), eventually ventricular tachycardia or fibrillation. The combination of increased (atrial) arrhythmogenesis and inhibited atrioventricular conduction (for example paroxysmal atrial tachycardia) is said to be pathognomonic (i.e., diagnostic) of digoxin toxicity. An often described, but rarely seen, adverse effect of digoxin is a disturbance of color vision (mostly yellow and green) called xanthopsia. Digoxin has potentially dangerous interactions with verapamil, amiodarone, erythromycin, and epinephrine (as would be injected with a local anesthetic).

The main pharmacological effects of digoxin are on the heart. Extracardiac effects are responsible for some of the therapeutic and many of the adverse effects. It has mechanical effects as it increases myocardial contractility; however, the duration of the contractile response is just slightly increased. Overall, the heart rate is decreased, while blood pressure increases as the stroke volume is increased, leading to increased tissue perfusion. Myocardial efficiency is due to improved hemodynamics, and the ventricular function curve is improved.

Other, electrical effects are an initial brief increase in action potential, followed by a decrease as the $K^+$ conductance increases due to an increased intracellular amounts of $Ca^{2+}$ ions. The refractory period of the atria and ventricles is decreased, while it increases in the sinoatrial and AV nodes. A less negative resting membrane potential is made, leading to increased excitability. Other, more indirect effects are cholinomimetic because of vagal stimulation, giving rise to AV nodal delay.

The conduction velocity increases in the atria, but decreases in the AV node. The effect upon Purkinje fibers and ventricles is negligible. Automaticity is also increased, in the atria, AV node, Purkinje fibers and ventricles. ECG changes are increased PR interval, due to decreased AV conduction, and a decreased QT interval because of the altered duration of decreased action potential. Also, the T wave is inverted, accompanied by ST depression. It may cause AV junctional rhythm and ectopic beats (bigeminy) resulting in ventricular tachycardia and fibrillation. Slight vasodilation is seen in heart failure. This effect is contrary to effects that should be seen as a result of increased intracellular calcium levels, but this occurs since digoxin improves hemodynamics, which leads to restored angiotensin levels and decreased sympathetic discharge, causing indirect vasodilation. Digoxin also affects the kidney by increased renal blood flow and increased glomerular filtration rate. A mild diuretic effect is seen only in heart failure.

Digoxin binds to a site on the extracellular aspect of the α-subunit of the $Na^+/K^+$ ATPase pump in the membranes of heart cells (myocytes) and decreases its function. This causes an increase in the level of sodium ions in the myocytes, which leads to a rise in the level of intracellular calcium ions. This occurs because the sodium/calcium exchanger on the plasma membrane depends on a constant inward sodium gradient to pump out calcium. Digoxin decreases sodium concentration gradient and the subsequent calcium outflow, thus raising the calcium concentration in myocardiocytes and pacemaker cells.

Increased intracellular calcium lengthens phase 4 and phase 0 of the cardiac action potential, which leads to a decrease in heart rate. Increased amounts of $Ca^{2+}$ also leads to increased storage of calcium in the sarcoplasmic reticulum, causing a corresponding increase in the release of calcium during each action potential. This leads to increased contractility, the force of contraction, of the heart.

There is also evidence that digoxin increases vagal activity, thereby decreasing heart rate by slowing depolarization of pacemaker cells in the AV node. This negative chronotropic effect would therefore be synergistic with the direct effect on cardiac pacemaker cells. Digoxin is used widely in the treatment of various arrhythmias.

2. Digitoxin

Digitoxin has similar structure and effects to digoxin (though the effects are longer-lasting). Unlike digoxin (which is eliminated from the body via the kidneys), it is eliminated via the liver, so could be used in patients with poor or erratic kidney function. However, it is now rarely used in current Western medical practice. While several controlled trials have shown digoxin to be effective in a proportion of patients treated for heart failure, the evidence base for digitoxin is not as strong, although it is presumed to be similarly effective. Digitoxin exhibits similar toxic effects to the more commonly used digoxin, namely: anorexia, nausea, vomiting, diarrhea, confusion, visual disturbances, and cardiac arrhythmias. Antidigoxin antibody fragments, the specific treatment for digoxin poisoning, are also effective in serious digitoxin toxicity. The first structural analysis of digitoxin was performed in 1925, but the full structure with an exact determination of the sugar groups was not accomplished until 1962.

3. Other Cardiac Glycosides

Gitoxin ($C_{41}H_{64}O_{14}$) is a secondary glycoside derived from *Digitalis purpurea* used in medicine for coronary disease. Other cardiac glycosides include oleandrin, neriifolin, bufalin, marinobufagenin, cinobufagenin, UNBS1450 and lanatoside C.

B. RO 31-8220 and Other PKC Inhibitors

The role of PKC isoforms in signal transduction pathways involved in regulation of the cell cycle, apoptosis, angiogenesis, differentiation, invasiveness, senescence and drug efflux are well established. As such, there are attractive candidates in cancer therapy, and include such molecules as including midostaurin (PKC-412, CGP 41251, N-benzoylstaurosporine), UCN-01 (7-hydroxystaurosporine), bryostatin 1, perifosine, ilmofosine, Ro 32-0432, GO 6976, ISIS-3521 (CGP 64128A), the macrocyclic bis (indolyl) maleimides (LY-333531, LY-379196, LY-317615), 13-HODE, AEB-071, Annexin V, Aprinocarsen, ARC, bisphosphonate, BSP-A1/A2, Butein, Calphostin C, Chelerythrine, Curcumin, Daphnetin, Dexamethasone, Enzastaurin, Erbstatin, H-7, Hispidin, Hypocrellin A, hypercin, MT477, NPC 15437, PAP, PKC412, R8605, RK-286C, Rottlerin, ruboxistaurin, sotrastaurin, staurosporine, UCN-01, UCN-02, Vanicosides A and B, and Verbascoside.

RO 31-8220 is a particular protein kinase C inhibitor, with activity at other protein kinases ($IC_{50}$ values are 33, 3, 8, 15 and 38 nM for $PKG_\alpha$, MAPKAP-K1b, MSK1, $GSK3_\beta$ and S6K1 respectively). Activates JNK and glycogen synthase, and inhibits MAPK and ERK2, in rat adipocytes and L6 myotubes. Also inhibits voltage-dependent $Na^+$ channels in the micromolar range.

C. Bafetinib and Lyn Inhibitors

The tyrosine-protein kinase Lyn is a protein that in humans is encoded in humans by the LYN gene. Lyn is a member of the Src family of protein tyrosine kinases, which is mainly expressed in hematopoietic cells, in neural tissues liver, and adipose tissue. In various hematopoietic cells, Lyn has emerged as a key enzyme involved in the regulation of cell activation. In these cells, a small amount of LYN is associated with cell surface receptor proteins, including the B cell antigen receptor (BCR), CD40, or CD19.

Lyn has been described to have an inhibitory role in myeloid lineage proliferation. Following engagement of the B cell receptors, Lyn undergoes rapid phosphorylation and activation. LYN activation triggers a cascade of signaling events mediated by Lyn phosphorylation of tyrosine residues within the immunoreceptor tyrosine-based activation motifs (ITAM) of the receptor proteins, and subsequent recruitment and activation of other kinases including Syk, phosholipase Cγ2 (PLCγ2) and phosphatidyl inositol-3 kinase. These kinases provide activation signals, which play critical roles in proliferation, $Ca^{2+}$ mobilization and cell differentiation. Lyn plays an essential role in the transmission of inhibitory signals through phosphorylation of tyrosine residues within the immunoreceptor tyrosine-based inhibitory motifs (ITIM) in regulatory proteins such as CD22, PIR-B and FCγRIIb1. Their ITIM phosphorylation subsequently leads to recruitment and activation of phosphatases such as SHIP-1 and SHP-1, which further downmodulate signaling pathways, attenuate cell activation and can mediate tolerance. In B cells, Lyn sets the threshold of cell signaling and maintains the balance between activation and inhibition. Lyn thus functions as a rheostat that modulates signaling rather than as a binary on-off switch.

Lyn has also been implicated to have a role in the insulin signaling pathway. Activated Lyn phosphorylates insulin receptor substrate 1 (IRS1). This phosphorylation of IRS1 leads to an increase in translocation of Glut-4 to the cell membrane and increased glucose utilization. In turn, activation of the insulin receptor has been shown to increase autophosphorylation of Lyn suggesting a possible feedback loop. The insulin secretagogue, glimepiride (Amaryl®) activates Lyn in adipocytes via the disruption of lipid rafts. This indirect Lyn activation may modulate the extrapancreatic glycemic control activity of glimepiride. The investigational diabetes therapeutic MLR-1023 being developed by Melior Discovery, directly and specifically activates Lyn. MLR-1023-mediated Lyn activation results in increased insulin sensitization and thereby potentiation of insulin signaling.

Much of the current knowledge about Lyn has emerged from studies of genetically manipulated mice. Lyn deficient mice display a phenotype that includes splenomegaly, a dramatic increase in numbers of myeloid progenitors and monocyte/macrophage tumors. Biochemical analysis of cells from these mutants revealed that Lyn is essential in establishing ITIM-dependent inhibitory signaling and for activation of specific protein tyrosine phosphatases within myeloid cells.

A particular Lyn inhibitor, bafetinib (INNO-406) is a potent and selective dual Bcr-Abl/Lyn tyrosine kinase inhibitor with $IC_{50}$ of 5.8 nM and 19 nM, respectively.

Bafetinib blocks WT Bcr-Abl autophosphorylation and its downstream kinase activity with IC50 of 11 nM and 22 nM in K562 and 293T cells, respectively. Bafetinib suppresses the growth of the Bcr-Abl-positive cell lines including K562, KU812, and BaF3/wt cells potently without effects on the proliferation of the Bcr-Abl-negative U937 cell line. Moreover, bafetinib exhibits a dose-dependent antiproliferative effect against Bcr-Abl point mutant cell lines, such as BaF3/E255K cells. In Bcr-Abl+ leukemia cell lines, Bafetinib induces both caspase-mediated and caspase-independent cell death by blocking the phosphorylation of Bcr-Abl.

In Bcr-Abl-positive KU812 mouse model, bafetinib (0.2 mg/kg/day) significantly inhibits tumor growth, and completely inhibits tumor growth without adverse effects at 20 mg/kg/day. For Balb/c mice, bafetinib shows maximal tolerated dose of 200 mg/kg/d and bioavailability value (BA) of 32%. In a central nervous system (CNS) leukemia model bearing Ba/F3/wt bcr-ablGFP, Ba/F3/Q252H, or Ba/F3/M351T cells, combination treatment of Bafetinib (60 mg/kg) and cyclosporine A (CsA) (50 mg/kg) leads to more significant inhibition of leukemia growth in the brain than either Bafetinib or CsA alone.

Another Lyn inhibitor is a peptide, octadecanoyl-Tyr-Gly-Tyr-Arg-Leu-Arg-Arg-Lys-Trp-Glu-Glu-Lys-Ile-Pro-Asn-Pro-$NH_2$.

D. BRAF Inhibitors

BRAF is a human gene that makes a protein called B-Raf. The gene is also referred to as proto-oncogene B-Raf and v-Raf murine sarcoma viral oncogene homolog B1, while the protein is more formally known as serine/threonineprotein kinase B-Raf. The B-Raf protein is involved in sending signals inside cells, which are involved in directing cell growth. In 2002, it was shown to be faulty (mutated) in human cancers.

Drugs that treat cancers driven by BRAF have been developed. On Aug. 17, 2011, one of them, vemurafenib, was approved by FDA for treatment of late-stage melanoma as the first drug to come out of fragment-based drug discovery. Pharmaceutical companies are developing other inhibitors of mutated B-raf protein for anticancer use, More general B-raf inhibitors include GDC-0879, PLX 4032, PLX-4720, PLX 4734 and Sorafenib Tosylate.

II. Methods Of Treatment

In a particular aspect, the present invention provides methods for the treatment of melanoma. Treatment methods will involve administering to an individual having such a disease an effective amount of a composition containing a compound or compounds of the present invention. An effective amount is described, generally, as that amount sufficient to detectably and repeatedly to ameliorate, reduce, minimize or limit the extent of the disease or its symptoms. More specifically, it is envisioned that the treatment with a compound or compounds of the present invention kill cancer cells, inhibit their growth, reduce or inhibit metastasis, inhibit or reduce or delay recurrence, or otherwise provide clinical benefit. Also, combinations my reduce toxicity due to lower dosing and or reduced frequency of administration.

A. Melanoma

Melanoma is less common than other skin cancers. However, it is much more dangerous if it is not found early. It causes the majority (75%) of deaths related to skin cancer. Worldwide, doctors diagnose about 160,000 new cases of melanoma yearly. It is more common in women than in men. In women, the most common site is the legs and melanomas in men are most common on the back. It is particularly common among Caucasians, especially northern Europeans living in sunny climates. There are high rates of incidence in Australia, New Zealand, North America (especially Texas and Florida), Latin America, and Northern Europe, with a paradoxical decrease in southern Italy and Sicily. This geographic pattern reflects the primary cause, ultraviolet light (UV) exposure crossed with the amount of skin pigmentation in the population.

1. Early Signs

Early signs of melanoma are changes to the shape or color of existing moles or, in the case of nodular melanoma, the appearance of a new lump anywhere on the skin (such lesions should be referred without delay to a dermatologist). At later stages, the mole may itch, ulcerate or bleed. Early signs of melanoma are summarized by the mnemonic "ABCDE":

Asymmetry
Borders (irregular)
Color (variegated)
Diameter (greater than 6 mm (0.24 in), about the size of a pencil eraser)
Evolving over time These classifications do not, however, apply to the most dangerous form of melanoma, nodular melanoma, which has its own classifications:

Elevated above the skin surface
Firm to the touch
Growing

Metastatic melanoma may cause nonspecific paraneoplastic symptoms, including loss of appetite, nausea, vomiting and fatigue. Metastasis of early melanoma is possible, but relatively rare: less than a fifth of melanomas diagnosed early become metastatic. Brain metastases are particularly common in patients with metastatic melanoma. It can also spread to the liver, bones, abdomen or distant lymph nodes.

2. Development

The earliest stage of melanoma starts when the melanocytes begin to grow out of control. Melanocytes are found between the outer layer of the skin (the epidermis) and the next layer (the dermis). This early stage of the disease is called the radial growth phase, and the tumor is less than 1 mm thick. Because the cancer cells have not yet reached the blood vessels lower down in the skin, it is very unlikely that this early-stage cancer will spread to other parts of the body. If the melanoma is detected at this stage, then it can usually be completely removed with surgery. When the tumor cells start to move in a different direction—vertically up into the epidermis and into the papillary dermis—the behavior of the cells changes dramatically.

The next step in the evolution is the invasive radial growth phase, which is a confusing term; however, it explains the next step in the process of the radial growth, when individual cells start to acquire invasive potential. This step is important—from this point on the melanoma is capable of spreading. The Breslow's depth of the lesion is usually less than 1 mm (0.04 in), the Clark level is usually 2.

The following step in the process is the invasive melanoma—the vertical growth phase (VGP). The tumor attains invasive potential, meaning it can grow into the surrounding tissue and can spread around the body through blood or lymph vessels. The tumor thickness is usually more than 1 mm (0.04 in), and the tumor involves the deeper parts of the dermis. The host elicits an immunological reaction against the tumor (during the VGP), which is judged by the presence and activity of the tumor infiltrating lymphocytes (TILs). These cells sometimes completely destroy the primary tumor; this is called regression, which is the latest stage of the melanoma development. In certain cases, the primary tumor is completely destroyed and only the metastatic tumor is discovered.

3. Detection

Visual diagnosis of melanomas is still the most common method employed by health professionals. Moles that are irregular in color or shape are often treated as candidates of melanoma. The diagnosis of melanoma requires experience, as early stages may look identical to harmless moles or not have any color at all. People with a personal or family history of skin cancer or of dysplastic nevus syndrome (multiple atypical moles) should see a dermatologist at least once a year to be sure they are not developing melanoma. There is no blood test for detecting melanomas.

Many melanomas present themselves as lesions smaller than 6 mm in diameter; and all melanomas were malignant on day 1 of growth, which is merely a dot. An astute physician will examine all abnormal moles, including ones less than 6 mm in diameter. Seborrheic keratosis may meet some or all of the ABCD criteria, and can lead to false alarms among laypeople and sometimes even physicians. An experienced doctor can generally distinguish seborrheic keratosis from melanoma upon examination, or with dermatoscopy.

Total body photography, which involves photographic documentation of as much body surface as possible, is often used during follow-up of high-risk patients. The technique has been reported to enable early detection and provides a cost-effective approach (being possible with the use of any digital camera), but its efficacy has been questioned due to its inability to detect macroscopic changes. The diagnosis method should be used in conjunction with (and not as a replacement for) dermoscopic imaging, with a combination of both methods appearing to give extremely high rates of detection.

Melanoma is divided into the following types:
Lentigo maligna
Lentigo maligna melanoma
Superficial spreading melanoma
Acral lentiginous melanoma
Mucosal melanoma
Nodular melanoma
Polypoid melanoma
Desmoplastic melanoma
Amelanotic melanoma
Soft-tissue melanoma
Melanoma with small nevus-like cells
Melanoma with features of a Spitz nevus
Uveal melanoma Confirmation of the clinical diagnosis is achieved with a skin biopsy. This is usually followed up with a wider excision of the scar or tumor. Depending on the stage, a sentinel lymph node biopsy is done, as well, although controversy exists around trial evidence for this procedure. Treatment of advanced malignant melanoma is performed from a multidisciplinary approach.

4. Staging

Melanoma stages are listed below with their 5 year survival rates:

Stage 0: Melanoma in situ (Clark Level I), 99.9% survival
Stage I/II: Invasive melanoma, 85-99% survival
T1a: Less than 1.00 mm primary tumor thickness, without ulceration, and mitosis<1/mm$^2$
T1b: Less than 1.00 mm primary tumor thickness, with ulceration or mitoses≥1/mm$^2$
T2a: 1.00-2.00 mm primary tumor thickness, without ulceration
Stage II: High risk melanoma, 40-85% survival
T2b: 1.00-2.00 mm primary tumor thickness, with ulceration
T3a: 2.00-4.00 mm primary tumor thickness, without ulceration
T3b: 2.00-4.00 mm primary tumor thickness, with ulceration
T4a: 4.00 mm or greater primary tumor thickness without ulceration
T4b: 4.00 mm or greater primary tumor thickness with ulceration
Stage III: Regional metastasis, 25-60% survival
N1: Single positive lymph node
N2: Two to three positive lymph nodes or regional skin/in-transit metastasis
N3: Four positive lymph nodes or one lymph node and regional skin/in-transit metastases
Stage IV: Distant metastasis, 9-15% survival
M1a: Distant skin metastasis, normal LDH
M1b: Lung metastasis, normal LDH
M1c: Other distant metastasis or any distant metastasis with elevated LDH 5. Prognosis Features that affect prognosis are tumor thickness in millimeters (Breslow's depth), depth related to skin structures (Clark level), type of melanoma, presence of ulceration, presence of lymphatic/perineural invasion, presence of tumor-infiltrating lymphocytes (if present, prognosis is better), location of lesion, presence of satellite lesions, and presence of regional or distant metastasis. Certain types of melanoma have worse prognoses but this is explained by their thickness. Interestingly, less invasive melanomas even with lymph node metastases carry a better prognosis than deep melanomas without regional metastasis at time of staging. Local recurrences tend to behave similarly to a primary unless they are at the site of a wide local excision (as opposed to a staged excision or punch/shave excision) since these recurrences tend to indicate lymphatic invasion.

When melanomas have spread to the lymph nodes, one of the most important factors is the number of nodes with malignancy. Extent of malignancy within a node is also important; micrometastases in which malignancy is only microscopic have a more favorable prognosis than macrometastases. In some cases micrometastases may only be detected by special staining, and if malignancy is only detectable by a rarely employed test known as the polymerase chain reaction (PCR), the prognosis is better. Macrometastases in which malignancy is clinically apparent (in some cases cancer completely replaces a node) have a far worse prognosis, and if nodes are matted or if there is extracapsular extension, the prognosis is still worse.

When there is distant metastasis, the cancer is generally considered incurable. The five year survival rate is less than 10%. The median survival is 6 to 12 months. Treatment is palliative, focusing on life-extension and quality of life. In some cases, patients may live many months or even years with metastatic melanoma (depending on the aggressiveness of the treatment). Metastases to skin and lungs have a better prognosis. Metastases to brain, bone and liver are associated with a worse prognosis.

There is not enough definitive evidence to adequately stage, and thus give a prognosis for ocular melanoma and melanoma of soft parts, or mucosal melanoma (e.g., rectal melanoma), although these tend to metastasize more easily. Even though regression may increase survival, when a melanoma has regressed, it is impossible to know its original size and thus the original tumor is often worse than a pathology report might indicate.

6. Treatment

Excisional biopsies may remove the tumor, but further surgery is often necessary to reduce the risk of recurrence. Complete surgical excision with adequate surgical margins and assessment for the presence of detectable metastatic disease along with short- and long-term follow-up is standard. Often this is done by a wide local excision (WLE) with 1 to 2 cm margins. Melanoma-in-situ and lentigo malignas are treated with narrower surgical margins, usually 0.2 to 0.5 cm. Many surgeons consider 0.5 cm the standard of care for standard excision of melanoma-in-situ, but 0.2 cm margin might be acceptable for margin controlled surgery (Mohs surgery, or the double-bladed technique with margin control). The wide excision aims to reduce the rate of tumor recurrence at the site of the original lesion. This is a common pattern of treatment failure in melanoma. Considerable research has aimed to elucidate appropriate margins for excision with a general trend toward less aggressive treatment during the last decades.

Mohs surgery has been reported with cure rate as low as 77% and as high as 98% for melanoma-in-situ. CCPDMA and the "double scalpel" peripheral margin controlled surgery is equivalent to Mohs surgery in effectiveness on this "intra-epithelial" type of melanoma.

Melanomas that spread usually do so to the lymph nodes in the area of the tumor before spreading elsewhere. Attempts to improve survival by removing lymph nodes surgically (lymphadenectomy) were associated with many complications, but no overall survival benefit. Recently, the technique of sentinel lymph node biopsy has been developed to reduce the complications of lymph node surgery while allowing assessment of the involvement of nodes with tumor.

Although controversial and without prolonging survival, sentinel lymph node biopsy is often performed, especially for T1b/T2+ tumors, mucosal tumors, ocular melanoma and tumors of the limbs. A process called lymphoscintigraphy is performed in which a radioactive tracer is injected at the tumor site to localize the sentinel node(s). Further precision is provided using a blue tracer dye, and surgery is performed to biopsy the node(s). Routine hematoxylin and eosin (H&E) and immunoperoxidase staining will be adequate to rule out node involvement. Polymerase chain reaction (PCR) tests on nodes, usually performed to test for entry into clinical trials, now demonstrate that many patients with a negative sentinel lymph node actually had a small number of positive cells in their nodes. Alternatively, a fine-needle aspiration biopsy may be performed and is often used to test masses.

If a lymph node is positive, depending on the extent of lymph node spread, a radical lymph node dissection will often be performed. If the disease is completely resected, the patient will be considered for adjuvant therapy. Excisional skin biopsy is the management of choice. Here, the suspect lesion is totally removed with an adequate (but minimal, usually 1 or 2 mm) ellipse of surrounding skin and tissue. To avoid disruption of the local lymphatic drainage, the preferred surgical margin for the initial biopsy should be narrow (1 mm). The biopsy should include the epidermal, dermal, and subcutaneous layers of the skin. This enables the histopathologist to determine the thickness of the melanoma by microscopic examination. This is described by Breslow's thickness (measured in millimeters). However, for large lesions, such as suspected lentigo maligna, or for lesions in surgically difficult areas (face, toes, fingers, eyelids), a small punch biopsy in representative areas will give adequate information and will not disrupt the final staging or depth determination. In no circumstances should the initial biopsy include the final surgical margin (0.5 cm, 1.0 cm, or 2 cm), as a misdiagnosis can result in excessive scarring and morbidity from the procedure. A large initial excision will disrupt the local lymphatic drainage and can affect further lymphangiogram-directed lymph node dissection. A small punch biopsy can be used at any time where for logistical and personal reasons a patient refuses more invasive excisional biopsy. Small punch biopsies are minimally invasive and heal quickly, usually without noticeable scarring.

High-risk melanomas may require adjuvant treatment, although attitudes to this vary in different countries. In the United States, most patients in otherwise good health will begin up to a year of high-dose interferon treatment, which has severe side effects, but may improve the patient's prognosis slightly. However British Association of Dermatologist guidelines on melanoma state that interferon is not recommended as a standard adjuvant treatment for melanoma. A 2011 meta-analysis showed that interferon could lengthen the time before a melanoma comes back but increased survival by only 3% at 5 years. The unpleasant side effects also greatly decrease quality of life. In Europe, interferon is usually not used outside the scope of clinical trials.

Metastatic melanomas can be detected by X-rays, CT scans, MRIs, PET and PET/CTs, ultrasound, LDH testing and photoacoustic detection. Various chemotherapy agents also are used, including dacarbazine (also termed DTIC), immunotherapy (with interleukin-2 (IL-2) or interferon (IFN)), as well as local perfusion, are used by different centers. The overall success in metastatic melanoma is quite limited. IL-2 (Proleukin) is the first new therapy approved for the treatment of metastatic melanoma in 20 years. Studies have demonstrated that IL-2 offers the possibility of a complete and long-lasting remission in this disease, although only in a small percentage of patients. A number of new agents and novel approaches are under evaluation and show promise. Clinical trial participation should be considered the standard of care for metastatic melanoma.

For lentigo maligna treatment, standard excision is still being performed by most surgeons. Unfortunately, the recurrence rate is exceedingly high (up to 50%). This is due to the ill-defined visible surgical margin, and the facial location of the lesions (often forcing the surgeon to use a narrow surgical margin). The narrow surgical margin used, combined with the limitation of the standard "bread-loafing" technique of fixed tissue histology, result in a high "false negative" error rate, and frequent recurrences. Margin control (peripheral margins) is necessary to eliminate the false negative errors. If bread loafing is used, distances from sections should approach 0.1 mm to assure that the method approaches complete margin control.

Some melanocytic nevi and melanoma-in-situ (lentigo maligna) have resolved with an experimental treatment: imiquimod (Aldara) topical cream, an immune enhancing agent. Some dermasurgeons are combining the 2 methods: surgically excising the cancer and then treating the area with Aldara cream postoperatively for three months.

Radiation therapy is often used after surgical resection for patients with locally or regionally advanced melanoma or for patients with unresectable distant metastases. It may reduce the rate of local recurrence but does not prolong survival. Radioimmunotherapy of metastatic melanoma is currently under investigation. Radiotherapy has a role in the palliation of metastatic melanoma.

B. Dosages

In certain embodiments, the compound or compounds of the present invention is/are administered to a subject. In another embodiment of the invention, the dose range of the compound(s) will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for a compound or compounds of the present invention.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

C. Formulations and Routes for Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain particular embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

D. Combined Therapy

In the context of the present invention, it is contemplated that the compounds may be used in combination with each other to more effectively treat melanoma. When multiple therapeutic agents are administered, as long as the dose of the additional therapeutic agent does not exceed previously quoted toxicity levels, the effective amounts of the additional therapeutic agent may simply be defined as that amount effective to exert a therapeutic effect when administered to an animal in combination with the primary agent. This may be easily determined by monitoring the animal or patient and measuring those physical and biochemical parameters of health and disease that are indicative of the success of a given treatment. Such methods are routine in animal testing and clinical practice.

To kill or slow the growth of a cancer cell using the methods and compositions of the present invention, one can provide to the subject a combination of agents. These compositions would be provided in a combined amount effective to effect a therapeutic benefit (inhibition of cancer cell growth, reduction in tumor size, induction of apoptosis in a cancer cell, etc.). This process may involve administering a combination at the same time. This may be achieved by administering a single composition or pharmacological formulation that includes both agents, or by administering two distinct compositions or formulations, at the same time.

Alternatively, treatment with one agent may precede or follow the additional agent treatment by intervals ranging from minutes to weeks. In embodiments where the additional agent is administered separately to the patient, one would generally ensure that a significant period of time did not expire between the time of each delivery, such that the agents would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either or both agents will be desired. Various combinations may be employed, where a BRAF inhibitor is "A" and the other agent is "B," as exemplified below:

A/B/A B/A/B B/B/A A/A/B B/A/A A/B/B B/B/B/A B/B/ A/B A/A/B/B A/B/A/B A/B/B/A B/B/A/A B/A/B/A B/A/ A/B B/B/B/A A/A/A/B B/A/A/A A/B/A/A A/A/B/A A/B/ B/B B/A/B/B B/B/A/B

E. Additional Combinations

Additional combinations with the agents/combinations set out above also are contemplated. Agents or factors suitable for use in a further combined cancer therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact a tumor or tumor cells with an agent according to the present invention along with the second agent or therapy. This may be achieved by irradiating the localized tumor site with radiation such as X-rays, UV-light, γ-rays or even microwaves. Alternatively, the tumor or tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a compound according to the present invention.

Agents that directly cross-link nucleic acids, specifically DNA, are envisaged to facilitate DNA damage leading to a synergistic, antineoplastic combination with compounds of the present invention. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

5-FU has been the first-choice chemotherapy drug for colorectal cancer for many years. It is used in combination with leucovorin (a vitamin), which makes 5-FU more effective. Recently, a pill form of 5-FU has been developed, called Xeloda®, which is used for colorectal cancer that has spread to other organs. Xeloda® is also being used as neoadjuvant therapy with radiation in patients with rectal cancers to heighten the effect of radiation.

Several new chemotherapy drugs also are used for the treatment of colorectal cancer that has spread. These include Camptosar®, Eloxatin®, Avastin®, Erbitux®, and Vectibix®. Camptosar®, Eloxatin®, and Avastin® are usually given along with 5-FU for metastatic colorectal cancer. Erbitux® is administered intravenously either alone or with Camptosar®. Vectibix® is usually given in combination with 5-FU and leucovorin.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials And Methods

Tissue and tumor cell preparation. Melanoma specimens were obtained with informed consent from patients with clinically apparent melanoma disease (biopsy-proven stage II, III, or IV, or obvious clinical stage IV) from which a small (typically 2-5 mm) tissue sample not required for standard-of-care pathology assessment was obtained. Most of the melanomas in this study were regional stage III lymph node or skin/soft tissue disease with palpable, clinically enlarged node(s) or soft tissues, undergoing definitive surgical resection, with biopsy-proven (most often needle core) diagnosis confirmed before surgery. Tumors were mechanically dissociated with a McIlwain tissue chopper (Mickle Laboratory Engineering) before sequential enzymatic digestion in 200 U/ml collagenase IV (Worthington) for 20 min followed by 0.05% trypsin-EGTA for 2 min, both at 37° C. DNase (50-100 U/mL) was added to reduce clumping of cells during digestion. Cells were filtered (40 µm cell strainer) to obtain a single cell suspension. Dead cells and debris were depleted by density centrifugation (1.1 g/ml Optiprep; Sigma) when necessary. Cells were always passaged in vivo (in immunocompromised mice as detailed below), not in vitro.

For analysis of circulating melanoma cells, blood was collected from each mouse by cardiac puncture, using a syringe pre-treated with citrate-dextrose solution (Sigma). Red blood cells were precipitated by Ficoll sedimentation following the manufacturer's instructions (Ficoll Paque Plus, GE Healthcare). Remaining cells were washed with HBSS (Invitrogen) prior to antibody staining and flow cytometric analysis.

All antibody staining was carried out for 20 min on ice, followed by washing and centrifugation. In order to select live human melanoma cells and to exclude endothelial and hematopoietic cells, tumors obtained directly from patients were stained with directly conjugated antibodies to human CD45 (HI30-APC; BD Biosciences), human CD31 (WM59-APC; eBiosciences), Glycophorin A (HIR2-APC; Biolegend) and HLA-A,B,C (G46-2.6-PE; BD Biosciences). Tumors or blood obtained from mice were stained with antibodies against mouse CD45 (30-F11-APC; eBiosciences), mouse CD31 (390-APC; Biolegend), mouse Ter119 (TER-119-APC; eBiosciences) and human HLA-A,B,C (G46-2,6-PE; BD Biosciences). Cells were resuspended in 10 µg/ml DAPI (Sigma) and sorted on a FACSAria (Becton Dickinson).

Transplanting melanoma cells. After sorting, cells were counted and resuspended in staining medium (L15 medium containing 1 mg/ml BSA, 1% penicillin/streptomycin and 10 mM HEPES [pH7.4]) with 25% high protein Matrigel (product 354248; BD Biosciences). Subcutaneous injections of human melanoma cells were performed in each flank and the interscapular region of NOD.CB17 (NOD/SCID IL2R$\gamma^{null}$, NSG) mice (Jackson Laboratories) in a final volume of 50 µl. These experiments were performed according to protocols approved by the animal use committees at the University of Michigan (protocol 9055) and the University of Texas Southwestern Medical Center (protocol 2011-0118).

Lentiviral transduction of human melanoma cells. Replication incompetent lentiviruses were generated by the cotransfection of 293T cells with three plasmids (fuw, vsv and delta). Forty-eight hours after transfection, supernatant with virus was collected and passed through a 0.45 µm low binding filter. Virus was concentrated by ultracentrifugation and aliquots were frozen at −80° C. until use. Around 150,000 sorted human melanoma cells (obtained directly from the patients or from xenografts) were incubated for 4 h at 37° C., 6.5% $CO_2$ in a well of an ultra-low attachment 24-well plate (Corning) containing 300 µl of cell culture medium (50% DMEM-low glucose, 30% Neurobasal (Invitrogen), 15% chick embryo extract, 1% Penicillin/Streptomycin, 1% non-essential amino acids (Gibco), 117 nM retinoic acid, 50 µM 2-mercaptoethanol (Sigma), 1% N2 supplement, 2% B27 supplement (Gibco), 20 ng/mL recombinant human bFGF, 20 ng/mL IGF-1 (R&D Systems)). 20 µl lentivirus and 10 µg/ml polybrene (Sigma) were added to the cultures. Cells were then washed twice with staining medium and approximately 25,000 cells (a mixture of infected and non-infected cells) were injected into NSG mice. After growing to 1-2 cm in diameter, tumors were excised, dissociated into a single cell suspension and luciferase-GFP+ cells were collected by flow cytometry for injections into secondary recipients. Metastasis was monitored by BLI in these secondary recipients.

Bioluminescence imaging (BLI). Mice were injected with 100 luciferase-GFP+ cells on the right flank and monitored until tumor diameters approached 20 mm, at which point they were imaged along with an uninjected control mouse on an IVIS Imaging System 200 Series (Calliper Life Sciences) using Living Image software. Mice were injected intraperitoneally with 100 µl of PBS containing 40 mg/ml D-luciferin monopotassium salt (Biosynth) ten minutes before imaging, followed by general anesthesia two minutes before imaging. Following imaging of the whole mouse, the mice were euthanized, and individual organs were quickly imaged. The exposure time of images ranged from 10 to 60 seconds. The bioluminescence signal was quantified using "region of interest" measurement tools in Living Image software. After imaging, tumors and organs were fixed in 10% neutral buffered formalin for histopathology.

Histopathology and immunostaining. Melanomas and mouse organs were fixed in 10% neutral buffered formalin, paraffin embedded, sectioned, and stained with hematoxylin and eosin for histopathology. Sections from paraffin-embedded tumors were stained for S100 and analysed by a dermatopathologist to confirm they were melanomas. Binding of anti-S100 antibody (DAKO) was carried out for 30 min at room temperature, detected by anti-rabbit secondary antibody (30 min at room temperature) and revealed using DAB chromagen after quenching endogenous peroxidases. Slides were counterstained with hematoxylin.

Example 2

Results

Figure 1A:
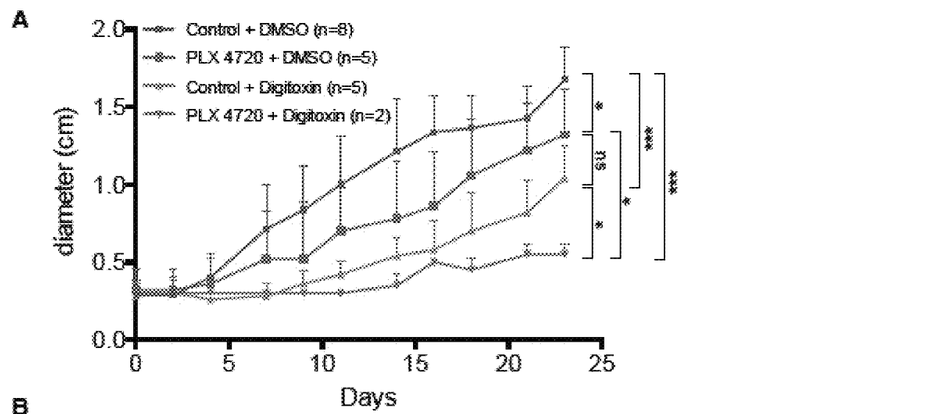
Figure 1B:
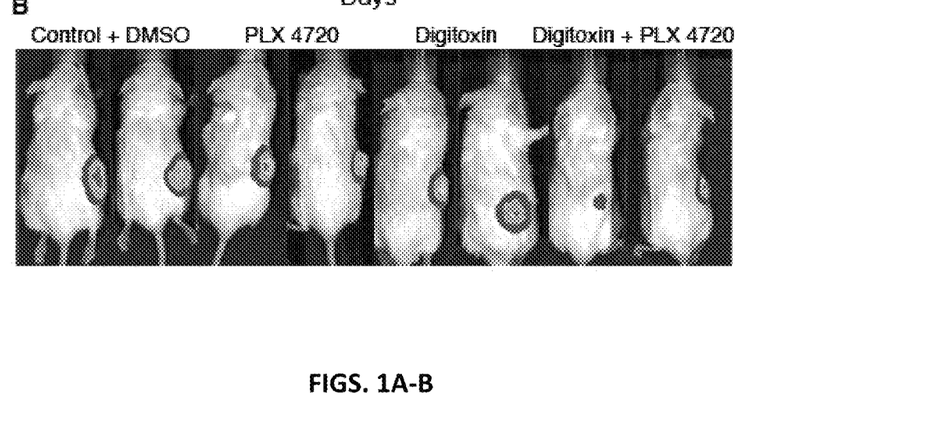
FIG. 1B, Representative bioluminescence images of melanomas at day 14.
Figure 2A:
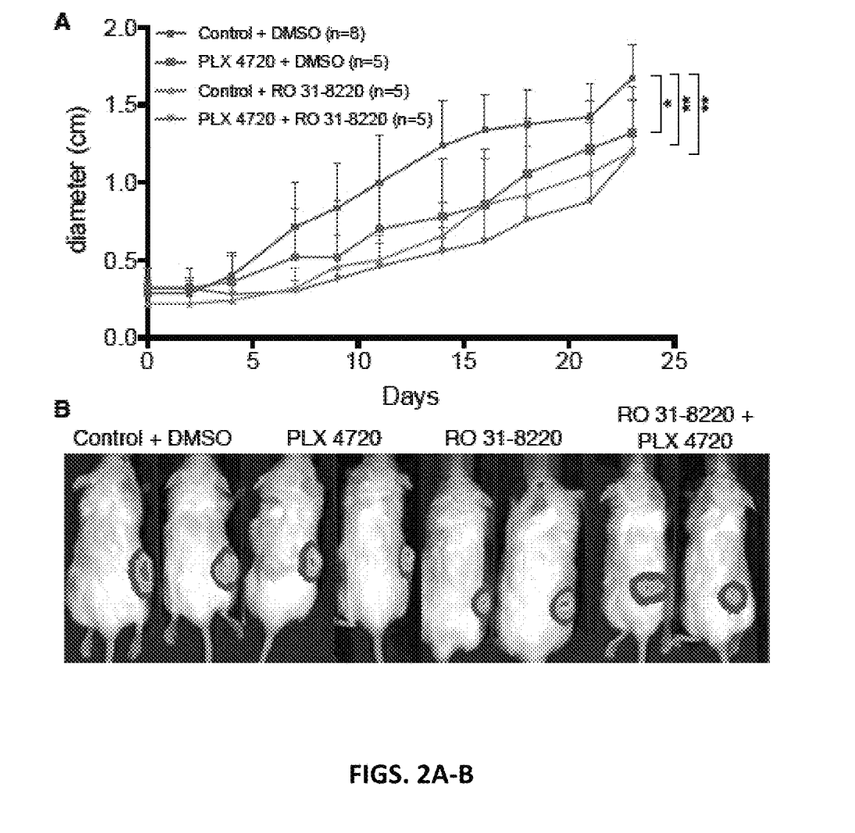
FIG. 2A, M481 tumor-growth curves of RO 31-8220 and/or BRAF inhibitor (PLX 4720) treated mice. M481 metastatic melanoma cells were implanted in s.c. tissue on right flanks of NSG mice. When tumors became palpable mice were i.p. injected with RO 31-8220 (3 mg/kg) or DMSO. For PLX 4720 treatment mice were switched to either a chow diet containing 417 mg/kg PLX 4720 or the control chow containing no compound. Tumors were measured every 2-3 day with calipers. Mean±SD is reported (* $P<0.05$, ** $P<0.001$, all other comparisons are not significant; two-tailed Student's t test).

Evidence for a BRAF inhibitor/cardiac glycoside in the blocking melanoma growth in a xenograft mouse model. The effect of digitoxin on in vivo tumor growth was tested in xenograft assays. In these experiments metastatic melanoma cells were implanted in s.c. tissue on right flanks of NSG mice. When tumors became palpable, mice were i.p. injected with digitoxin (0.5 mg/kg) or DMSO. The efficacy of these treatments was also tested in combination with a BRAF inhibitor (PLX 4720). For PLX 4720 treatment mice were switched to either a chow diet containing 417 mg/kg PLX 4720 or the control chow containing no compound. Tumors were measured every 2-3 day with calipers and bioluminescence imaging was performed at day 14. These pre-clinical mouse xenograft assays showed that digitoxin inhibited the growth of a melanoma better than BRAF inhibitor (PLX 4720) and the combination of digitoxin with PLX 4720 almost completely eradicated tumors (FIGS. 2A-B). These results suggest that cardiac glycosides are effective in the inhibition of melanoma either alone or in combination with BRAF inhibitors.

Evidence for BRAF inhibitor/PKC inhibitor (RO 31-8220) blocking melanoma growth in a xenograft mouse model. The effect of RO 31-8220 on in vivo tumor growth was tested in xenograft assays. In these experiments metastatic melanoma cells were implanted in s.c. tissue on right flanks of NSG mice. When tumors became palpable, mice were i.p. injected with RO 31-8220 (3 mg/kg) or DMSO. The efficacy of these treatments was also tested in combination with PLX 4720, as described above. Tumors were measured every 2-3 day with calipers and bioluminescent imaging was performed at day 14. These pre-clinical mouse xenograft assays showed that RO 31-8220 inhibited the growth of a melanoma as well as the BRAF inhibitor (PLX 4720) and the combination of RO 31-8220 with PLX 4720 was more effective than either agent alone. These results suggest that RO 31-8220 is effective in the inhibition of melanoma either alone or in combination with BRAF inhibitors (FIGS. 2A-B).

Evidence for a BRAFinhibitor/Lyn kinase inhibitor (Bafetinib) blocking melanoma growth in a xenograft mouse model. Since the efficacy of Bafetinib as a monotherapy for melanoma is unknown, the inventors set up drug treatments on xenografted NSG mice in combination with a BRAF inhibitor, PLX4720. Mice were switched to either a chow diet containing 417 mg/kg chow PLX4720 or the control chow containing no compound.

Figure 3A:
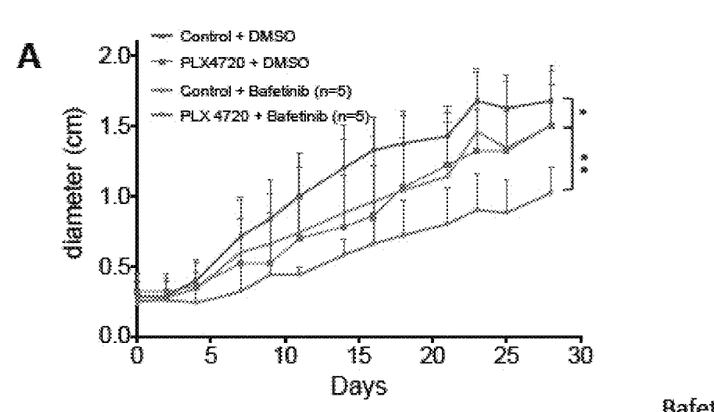
FIG. 3A, M481 tumor-growth curves of bafetinib and/or BRAF inhibitor (PLX 4720) treated mice. M481 metastatic melanoma cells were implanted in s.c. tissue on right flanks of NSG mice. When tumors became palpable mice were i.p. injected with bafetinib (4 mg/kg/day) or DMSO. For PLX4720 treatment mice were switched to either a chow diet containing 417 mg/kg PLX4720 or the control chow containing no compound. Tumors were measured every 2-3 day with calipers. Mean±SD is reported. (* $P<0.0001$, ** $P<0.005$; Two-tailed paired t-test.
Figure 3B:
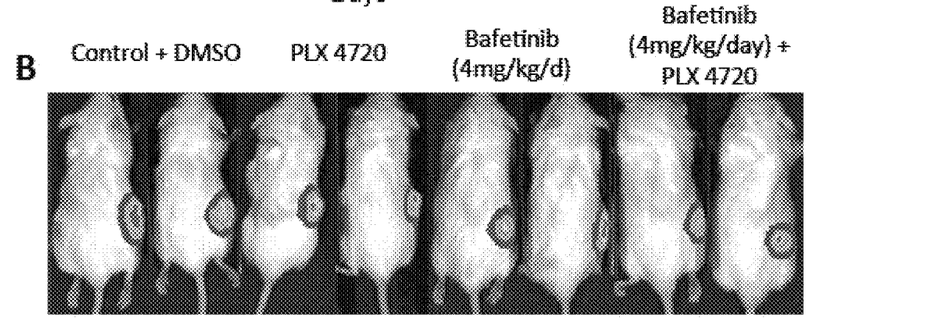
FIG. 3B, Representative bioluminescence images of melanomas at day 14.

The inventors observed a significant reduction in the growth of subcutaneous tumors treated with Bafetinib at 4 mg/kg/day alone, in comparison to the DMSO control (p-value<0.0001, two-tailed paired t-test), shown in FIG. 3A. Similarly, there was a significant reduction of tumor growth when mice were treated with the combination of PLX 4720 and 4 mg/kg/day of Bafetinib, compared to PLX 4720 alone (p-value<0.005, two-tailed paired t-test). They also confirmed the expression of the GFP-luciferase in control, monotherapy and combination treatment tumors, as shown in FIG. 3B.

Figure 4:
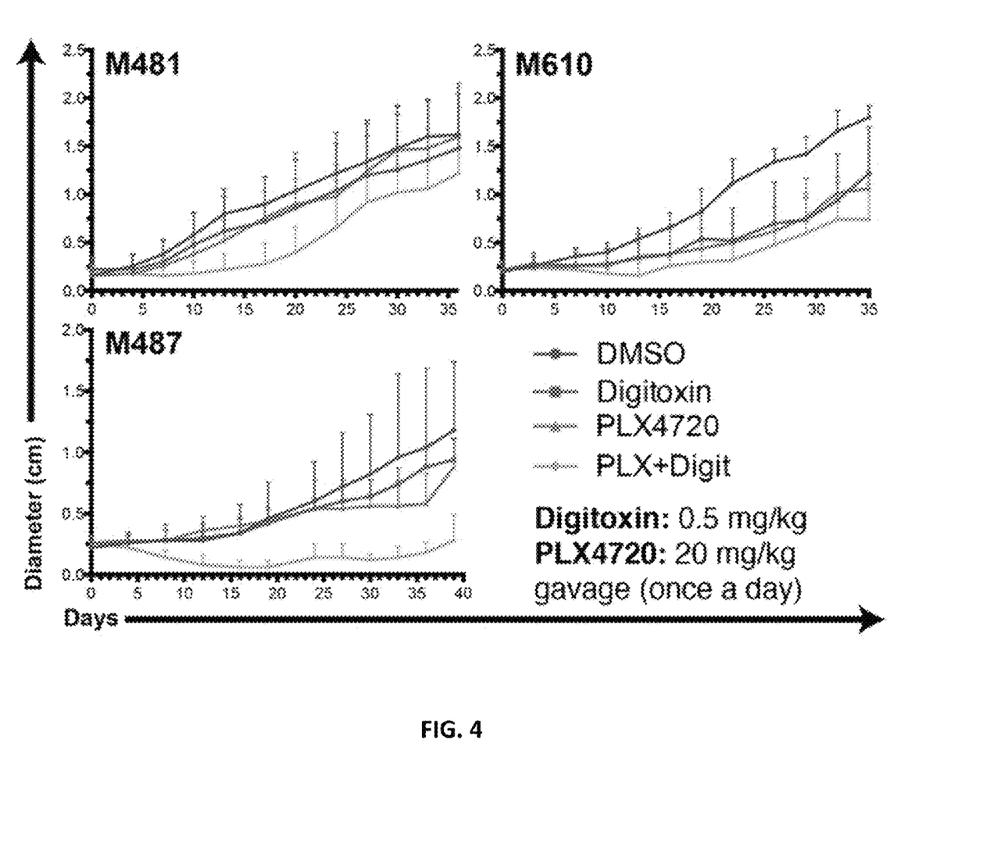

Effect of Digitoxin and/or PLX4720 on in vivo tumor growth using primary melanomas isolated from three patients. The inventors extended their observations to once-a-day oral delivery of digitoxin and/or PLX4720 on the growth of xenografted primary melanomas isolated from three patients. In these experiments metastatic melanoma cells were injected subcutaneously in the right flanks of immunocompromised NSG mice. When tumors became palpable, mice were randomized to four different treatments. Mice were treated either with digitoxin (0.5 mg/kg/day in 200 μl of 0.5% promethylcellulose, 0.2% Tween80 and 5% DMSO by oral gavage), or PLX4720 (20 mg/kg/day in 200 μl of 1% carboxymethyl cellulose and 5% DMSO by oral gavage) alone, or in combination. Control mice received vehicle only (200 μl 0.5% promethylcellulose, 0.2% Tween80 and 5% DMSO per day). Tumors were measured every 2-3 days with calipers. These mouse xenograft assays showed that digitoxin and PLX4720 individually slowed the growth of human melanoma xenografts. However, the combination of digitoxin and PLX4720 was more effective against all three tested melanomas (FIG. 4).

\* \* \*

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

IV. REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Remington's Pharmaceutical Sciences, 18th Ed. Mack Printing Company, 1990

What is claimed:

1. A method of inhibiting melanoma in a subject comprising administering to said subject:
   (a) a BRAF inhibitor selected from the group consisting of PLX 4032 and PLX 4720; and
   (b) digoxin or digitoxin,
   in an amount sufficient to inhibit said melanoma.
2. The method of claim 1, wherein said subject is a human.
3. The method of claim 1, wherein said subject is a non-human mammal.
4. The method of claim 1, wherein inhibiting comprises inhibiting the growth of primary melanomas, inhibiting the formation of metastases, inhibiting the growth of metastases, killing circulating melanoma cells, inducing remission, extending remission, or inhibiting recurrence.
5. The method of claim 1, wherein said melanoma is AJCC stage III disease.
6. The method of claim 1, wherein said melanoma is AJCC stage IV disease.
7. The method of claim 1, wherein said subject has previously received another therapy selected from the group consisting of a radiotherapy, a chemotherapy, an immunotherapy, a molecularly targeted therapy or had surgical resection of a tumor.
8. The method of claim 7, wherein said BRAF inhibitor and digoxin or digitoxin are administered before the or after the other therapy.
9. The method of claim 7, wherein said BRAF inhibitor and digoxin or digitoxin are administered at the same time as the other therapy.
10. The method of claim 1, wherein said BRAF inhibitor is PLX 4720 and the cardiac glycoside is digitoxin.
11. The method of claim 1, wherein said BRAF inhibitor is administered more than once.
12. The method of claim 1, wherein said digoxin or digitoxin is administered more than once.
13. The method of claim 1, wherein said digoxin is administered.
14. The method of claim 1, wherein administering comprises intravenous, intraarterial, subcutaneous, oral or intratumoral administration.
15. The method of claim 1, wherein administering comprises local, regional or systemic administration, or comprises continuous infusion over a period of time.
16. The method of claim 1, wherein said digitoxin is administered.
17. The method of claim 1, wherein said subject has failed one or more standard melanoma therapies.
18. The method of claim 1, wherein said amount sufficient to inhibit said melanoma is less than the amount required for inhibition by any single agent alone.

19. The method of claim 1, wherein said amount sufficient to inhibit said melanoma is less toxic than the amount required for inhibition by any single agent alone.

* * * * *

UNITED STATES PATENT AND TRADEMARK OFFICE
CERTIFICATE OF CORRECTION

PATENT NO. : 9,561,245 B2  
APPLICATION NO. : 14/019327  
DATED : February 7, 2017  
INVENTOR(S) : Sean Morrison et al.

Page 1 of 1

It is certified that error appears in the above-identified patent and that said Letters Patent is hereby corrected as shown below:

In the Claims

In Claim 8, Column 24, Line 42, delete "before the or" and insert --before or-- therefor.

Signed and Sealed this
Sixteenth Day of May, 2017

Michelle K. Lee
*Director of the United States Patent and Trademark Office*